US006787137B1

(12) United States Patent
Jacobs et al.

(10) Patent No.: US 6,787,137 B1
(45) Date of Patent: Sep. 7, 2004

(54) CAMPYLOBACTER VACCINE

(75) Inventors: Antonius Arnoldus Christiaan Jacobs, Kessel (NL); Johannes Franciscus van den Bosch, Boxmeer (NL); Petrus Johannes Maria Nuijten, Boxmeer (NL)

(73) Assignee: Akzo Nobel N. V., Arnhem (NL)

( * ) Notice: Subject to any disclaimer, the term of this patent is extended or adjusted under 35 U.S.C. 154(b) by 0 days.

(21) Appl. No.: 09/544,683

(22) Filed: Apr. 7, 2000

(30) Foreign Application Priority Data

Apr. 9, 1999 (EP) ............................................ 99201086

(51) Int. Cl.[7] ............................................ A61K 39/395

(52) U.S. Cl. ................................ 424/164.1; 424/157.1; 424/165.1; 424/202.1; 424/203.1; 424/204.1; 424/234.1; 424/244.1; 424/130.1; 424/178.1; 424/158.1; 424/159.1; 424/161.1; 530/387.1; 530/350

(58) Field of Search ........................... 424/157.1, 165.1, 424/164.1, 202.1, 203.1, 204.1, 234.1, 244.1, 178.1, 130.1, 158.1, 159.1, 161, 135.1, 184.1, 87, 161.1, 252.1; 530/387.1, 350, 388.1, 833, 389.5; 514/2, 21; 435/912, 6, 325

(56) References Cited

U.S. PATENT DOCUMENTS

| | | | | | |
|---|---|---|---|---|---|
| 4,748,018 | A | * | 5/1988 | Stolle et al. | 424/87 |
| 5,470,958 | A | * | 11/1995 | Blaser et al. | 530/389.5 |
| 5,827,654 | A | | 10/1998 | Chan et al. | |
| 5,871,731 | A | * | 2/1999 | Sprotte et al. | 424/130.1 |
| 5,874,300 | A | * | 2/1999 | Blaser et al. | 435/325 |
| 6,020,125 | A | * | 2/2000 | Chan et al. | 435/6 |
| 6,077,678 | A | * | 6/2000 | Pace et al. | 435/7.1 |
| 6,087,105 | A | * | 7/2000 | Chan et al. | 435/6 |
| 6,156,546 | A | * | 12/2000 | Konkel et al. | 435/91.2 |

OTHER PUBLICATIONS

Torres, O et al, Acta Paediatr., vol. 82, pp. 835–888, 1993, Protedtion against Campylobacter diarrhea:role of milk IgA antibodies against bacterial surface antigens.*

Glenn–Calvo, E. et al, FEMS Microbiology Letters, vol. 123, pp. 299–304, 1994, Isolation and characterization of the flagellar hook of Campylobacter jejuni.*

Blaser, MJ et al, Infection Immunity, vol. 53(1), Jul. 1986, p. 47–52.*

Blaser, MJ et al, Journal of Infectious Diseases, vol. 167(2), p. 372–377, Feb. 1993.*

Dolby, JM et al, J. Hyg. Camb. vol. 96, pp. 143–151, 1986.*

Cawthraw, S et al, Avian Diseases, Apr.–Jun. 1994, vol. 38(2), pp. 341–349.*

Kervella, M et al, Infection Immunity, Aug. 1993, vol. 61(8), pp. 3440–3448.*

(List continued on next page.)

*Primary Examiner*—Lynette R. F. Smith
*Assistant Examiner*—Ginny Allen Portner
(74) *Attorney, Agent, or Firm*—William P. Ramey; William M. Blackstone

(57) ABSTRACT

The present invention relates to vaccines comprising antiserum raised against a flagellaless Campylobacter strain for the prevention of Campylobacter colonisation in animals. The invention also relates to antigenic Campylobacter proteins visible in a Western blot of *Campylobacter jejuni* protein after incubation of said Western blot with antibodies against a flagellaless mutant of *Campylobacter jejuni* and not visible after incubation of said blot with antibodies against wild type *Campylobacter jejuni*, and to their use in vaccines and the manufacturing thereof. The invention further relates to vaccines comprising such proteins and antibodies against such proteins. The invention further relates to the use of such Campylobacter proteins and to antiserum and antibodies raised against Campylobacter antigens for the preparation of vaccines. Finally, the invention relates to methods for the preparation of such vaccines.

4 Claims, 3 Drawing Sheets

OTHER PUBLICATIONS

Winsor, DK et al, Gastroenterology, vol. 90(5 pt. 1), pp. 1217–1222), May 1986.*
Wassenaar, Trudy M., Clinical Microbiology Review, Jul. 1997, pp. 466–476, vol. 10(3).*
Wassenaar, TM et al, The EMBO Journal, vol. 10(8), pp. 2055–2061, 1991.*
Guerry, P, Journal of Infectious Diseases, vol. 176(suppl. 2) pp. S112–S124, Dec. 1997.*
Wirguin, I et al, Annals of neurology, Jun. 1994, vol. 35(6), pp. 698–703.*
Husu, J etal, Journal of Applied Bacteriolgoy, vol. 74(5), pp. 564–569, 1993.*
Heaton, P, Lancet, vol. 341(8851), p. 1036, Apr. 17, 1993.*
Berg, RL et al, Am. J. Vet. Res., vol. 40(1), pp. 21–25, 1979.*
Diaz, BA et al, VI th International Workshop on Campylobacter Helicobacter and Related organisms, Sydney, New South Wales, Australia, Oct. 7–10, 1991, Microb. Ecol. Health Dis, vol. 4(spec. issue) p. S25, 1991.*
Grant, CCCR etal, Infection and Immunity, vol. 61(5), pp. 1764–1771, May 1993.*
Griffiths, PL et al, Journal of Applied Bacteriology, 1992, vol. 72(6), pp. 467–474.*
Guerry, P et al, Journal of Bacteriology, vol. 172(4), pp. 1853–1860, Apr. 1990.*
Kinsella, N et al, Journal of Bacteriology, vol. 179(15), pp. 4647–4653 1997.*
Nachamkin, I et al, Applied and Environmental Microbiology, vol. 59(5), pp. 1269–1273, May 1993.*
Page, WJ et al, Journal of General Microbiology, vol. 134(pt 11), Nov. 1988, pp. 2925–2932.*
Russell, RG etal, Infection and Immunity, Sep. 1994, vol. 62(9), pp. 3773–3779.*
Wirguin, I et al, Journal of Neuroimmuno ogy, vol. 78(1–2), pp. 138–142, Sep. 1997.*
Wassenaar, TM et al, Infection Immunity vol. 62(9), pp. 3901–3906, Sep. 1994.*
Wassenaar, TM etal, Journal of General Microbiology, vol. 139, pp. 1171–1175, 1993.*
Guerry, Patricia, The Journal of Infectious Diseases, 1997, vol. 176(suppl. 2), pp. S122–S124, Nonlipopolysaccharide surface antigens of Campylobacter species.*
Tsubokura, K et al, Clinical Experimental Immunology, vol. 108(3)1997, pp. 451–455, Oral administration of antibodies as prophylaxis and therapy in Campylobacter jejuni–infected chickens.*
Logan, SM et al, Infection and Immunity, vol. 38(1), pp. 898–906, 1982, Dec., Outer membrane characteristics of Campylobacter jejuni.*
Torres, O et al, ACTA Paediatr. vol. 82, pp. 835–838, 1993.*
Blaser, MJ et al, Infection and Immunity, vol. 53(1), pp. 47–53, Jul. 1986.*
Blaser, MJ et al, Infection and Immunity, vol. 42, pp. 276–284, 1983; only pp. 276–281 & 284 provided.*
Diker, KS et al, ACTA microbiologica Hungarica (Hungary), vol. 39(2), pp. 133–136, 1992.*
Dolby, JM et al, Journal of hygience, (England), Apr. 1986, vol. 96(2), pp. 143–151.*
Huyer, M et al, FEMS Microbiol Letter, vol. 37, pp. 247–250, 1986.*
McSweegan, E et al, Infection and Immunity, vol. 55(6), p. 1431–1435, Jun. 1987.*
Winsor et al, Am. Gastroent. Assoc., 1985.*
Winsor D K Jr. et al., "Western Blot Analysis of Intestinal Secretory Immumoglobulin A Response to Campylobacter Jejuni Antigens in Patients with Naturally Acquired Campylobacter Enteritis" Gastroenterology, vol. 90, No. 5, pt.1, May 1986.
Blaser M J et al., "Antigenicity of Campylobacter jejuni Flagella" Infect. Immun., vol. 53, No. 1, 1986.
Schwartz D et al., "Iron–regulated Proteins in Outer Membranes of Campylobacter jejuni diarrhoea Isolates and Immune Response to the Proteins in Patients" Aug. 1994 (abstract only).
Dolby J. M. et al., "The Protection of Infant Mice from Colonization with Campylobacter jejuni by Vaccination of the Dams" Journal of Hygiene, vol. 96, No. 2, Apr. 1986.
Wassenaar T. M. et al., "Colonization of Chicks by Motility Mutants of Campylobacter jejuni Demonstrates the Importance of Flagellin A Expression "Journal of General Microbiology, Jun. 1993.

* cited by examiner

CAMPYLOBACTER VACCINE

BACKGROUND OF THE INVENTION

1. Field of the Invention

The present invention relates to vaccines against Campylobacter colonisation, to the use of Campylobacter proteins and anti-Campylobacter antibodies for the preparation of such vaccines and to methods for the preparation of such vaccines.

2. Description of Related Art

Bacteria of the genus Campylobacter are Gram-negative spiral shaped pathogenic bacteria, with a high motility and carrying a flagellum at one or both poles of the cell. Several Campylobacter species have been found. *Campylobacter jejuni* is very often found in poultry. Frequently *Campylobacter coli* and (to a lesser extent) the recently found *Campylobacter hyoilei* are found in pigs.

Of these, *Campylobacter jejuni* is the most frequently isolated Campylobacter species in association with human diarrhoea. It is becoming more and more evident that the number of Campylobacter infections in humans exceeds the number of Salmonella infections. (Griffiths et al., Journ. of Applied Bacteriology 1990, 69: 281–301, Walker et al., Microbiological reviews 1986, 50: 81–94, Butzler, J-P., ISBN 0-8493-5446-3, RIVM Report No. 216852002, Bilthoven, the Netherlands). It is difficult to avoid infection in humans with Campylobacter since, first of all, Campylobacter is a food borne zoonotic bacterium for which many animals, both wild and domestic, healthy or sick serve as a reservoir. In addition the bacterium has many different routes of transmission. Bacteria can survive in a dormant coccal form for several weeks on e.g. the surface of carcasses and in water. The bacterium can therefore easily be transmitted to man through direct contact with animals or by means of contaminated water or food, e.g. milk or meat. *C. jejuni* is present in many healthy animals, e.g. avian species such as turkey and chicken, cattle, sheep, horses and rodents. Chicken meat, an important nutrient source in many countries world-wide is known to be very frequently contaminated with Campylobacter (Shane (1992), S. M., Avian Pathology 21: 189–213). This is not only the case in developing countries but also in e.g. Europe. Campylobacter resides in the gut of poultry. Contamination of the meat frequently happens in the slaughterhouse when the intestinal tract, which is often heavily Campylobacter-contaminated, is removed from the animal. Contamination during slaughter is very difficult to avoid. In the Netherlands, about 50% of the chicken meat is contaminated, in spite of the high hygienic standards applied in meat industry. A recent overview of the Epidemiology of Campylobacter in poultry is given in the Thesis of C. M. Karssen, (ISBN 90-71463-72-9). As a result of this high contamination pressure, about 300,000 persons annually in the Netherlands only (total population 15.000.000) suffer from Campylobacter infection, caused by handling or eating undercooked poultry meat. These figures are not significantly different in other European countries. World-wide, annually more than 400.000.000 cases are estimated to occur (Pace et al., Vaccine 1998, 16: 1563–1574). Campylobacter causes enteric infections in humans, and occasionally more severe diseases like abortion, meningitis, apendicitis, and urinary tract infection. (Blaser et al., New Engl. J. Med. 1981, 305: 1444–1452, Butzler et al., Clinics in Gastroenterol. 1979, 8: 737–765). Also, severe neurologic complications such as Guillain-Barré syndrome and Miller-Fisher syndrome are sometimes seen (Schwerer et al., 1995. , J. Endotox. Res. 2: 395–403 and Salloway et al., 1996, Infect. Immun. 64: 2945–2949). Diarrhoea due to *Campylobacter jejuni* is usually a self-limiting infection, lasting about 2–7 days. In young children, old people and immuno-compromised patients, the disease is not self-limiting and requires antibiotic treatment.

It is clear that, if a potential vaccine against Campylobacter for human use would be available, it could prevent humans from becoming infected. This would however require a standard vaccination comparable to vaccination against e.g. mumps and measles. This is evidently not practical. A more logical approach lies in avoiding the transmission from animal to man, specifically from poultry to man. The easiest way of doing this is by vaccinating poultry against Campylobacter infection. Vaccination of poultry (as well as human vaccination) has however turned out to be much more complicated than was initially expected. This is due to the fact that Campylobacter is, in spite of the fact that it colonises the gut, not pathogenic to poultry. Most vaccines tested are inactivated whole cell preparations, administered systemically or orally, sometimes in combination with adjuvants. In some cases colonisation of the gut could, to a certain extent, be decreased, but there are no examples of vaccines avoiding colonisation. Shedding of Campylobacter could not be stopped by any of these vaccines. Killed whole cell vaccines, if compared with subunit vaccines, have been considered the best candidates for a vaccine, because in principle they still possess all potential immunogenic determinants. Next to the development of whole cell vaccines, much effort has been put in the development of flagella-based subunit vaccines. Flagella have been recognised as the immunodominant antigen recognised during infection and numerous studies have suggested a role for this protein in protection (Martin et al., Inf. And Immun. 1989, 57: 2542–2546, Wenman et al., J. Clin. Microbiol. 1985, 21: 108–112). Flagella-less mutants are known not to colonise the gut, and they disappear from the infected animal within one or two weeks whereas the wild type bacterium remains present in the gut. Flagella are thus by far the most likely candidates for the preparation of a vaccine, especially since they seem to play a key role, if not the only role, in the colonisation of the gut. If colonisation could be prevented, that would be a first step in the elimination of contamination in poultry. Nevertheless, potential vaccines based upon the flagella of Campylobacter have not given an acceptable level of protection.

Next to active vaccination as described above, passive vaccination has been tested as a means of decreasing Campylobacter infection. Tsubokura et al (1997, Clin. Exp. Immunol. 108: 451–455) have orally administered antibodies against whole *Campylobacter jejuni* cells followed by challenge with *Campylobacter jejuni*. They claim a 1–2 log reduction in the number of bacteria found in the faeces of thus vaccinated chickens. All efforts made so far have not yet led to any vaccine, be it live, inactivated or on the basis of subunits, that is capable of significantly diminishing the level of colonisation and the amount of bacteria shedded in the faeces. It is clear, that there still is a need for a reliable and safe vaccine or alternative treatment.

In principle, there is no need to protect poultry against Campylobacter infection during their whole life span. They do not suffer from infection as explained above. Therefore, a treatment capable of diminishing the amount of bacteria and thus the infective pressure shortly before slaughter would be an efficient treatment for suppressing subsequent contamination of the meat during slaughter. And this in turn would prevent meat-transmitted human Campylobacter infection.

SUMMARY OF THE INVENTION

It is an objective of the present invention to provide a vaccine that is capable of both diminishing the level of colonisation and shedding, or even of eliminating Campylobacter from the caecum of poultry. This avoids Campylobacter-contamination of the meat during slaughtering and therefore avoids subsequent infection of humans.

It was surprisingly found now that a vaccine having these characteristics can be based upon antibodies against flagellaless mutants of Campylobacter. This is highly unexpected since, as mentioned above, flagella are considered to be the key protein involved in adherence and colonisation. Even more surprising, such a vaccine does diminish colonisation and shedding of wild type flagellated Campylobacter. This is the first time that a vaccine is reported that is even capable to eliminate Campylobacter from the ceca below the level of detection.

DESCRIPTION OF PREFERRED EMBODIMENT

Figure 1:
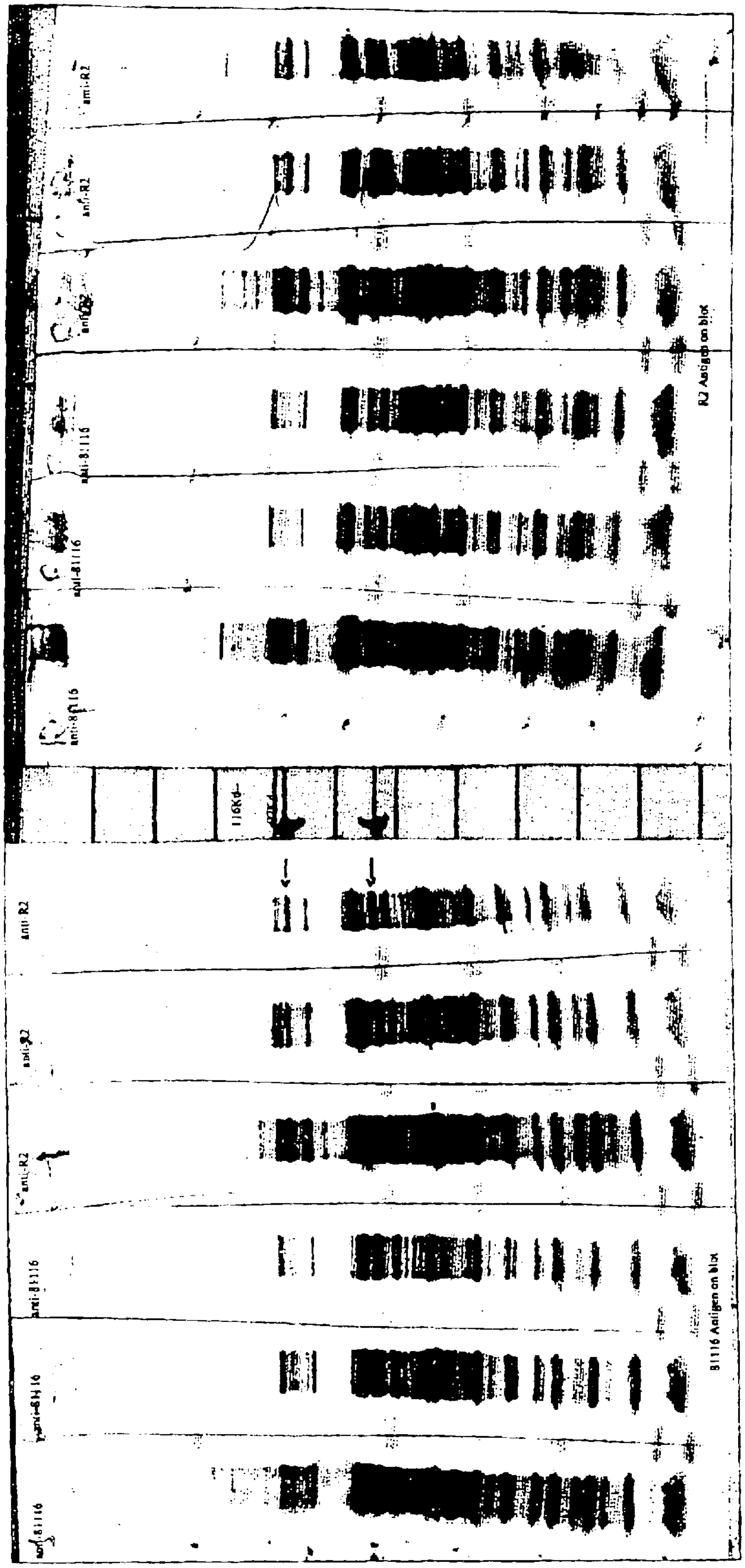
FIG. 1. Western blot comprising total antigen of wild type Campylobacter strain 81116 (left), and Western blot comprising antigen of flagellates Campylobacter strain 81116-2R. Lanes 1 and 7, and lanes 2 and 8, and lanes 3 and 9 were incubated with type Campylobacter strain 81116 respectively. Lanes 4 and 10, lanes 5 and 11, and lanes 6 and 12 were incubated with 20, 200 or 400 times diluted antiserum against flagellaless Campylobacter strain 81116-2R respectively.

One embodiment of the invention relates to vaccines for the prevention of Campylobacter colonisation in animals, which vaccines comprise antiserum against a flagellaless Campylobacter strain.

Such a vaccine can in a very simple form comprise just isolated antiserum against Campylobacter and possibly a diluent. Such a diluent can be added to dilute the antiserum if the amount of antibody titre is too high. The diluent can be as simple as distilled water, or physiological salt solution. Actually any pharmaceutically acceptable diluent can be used.

The invention is equally applicable for Campylobacter contamination in poultry, pigs and other animals.

Given however the very high contamination pressure of chicken meat, a preferred form of this embodiment relates to flagellaless Campylobacter strains of the species *Campylobacter jejuni*, and to poultry.

Any flagella-less Campylobacter strain can be used for raising antiserum. Especially those flagella-less Campylobacter strains that have growth-rates comparable to wild type strains are preferred. A very suitable flagella-less Campylobacter strain for raising antibodies has been described by Wassenaar, T. M., Bleumink-Pluym, N. M. C. and van der Zeijst, B. A. M. 1991, in the EMBO Journal 10:2055–2061.

Thus, in a preferred form, the flagella-less *Campylobacter jejuni* strain against which the antibodies are raised, is strain R2.

Antibodies suitable for use in a vaccine according to the present invention can be obtained from polyclonal sera, monospecific sera or from monoclonal antibody culture. Polyclonal sera have the advantage that they are easily made according to standard techniques. Techniques for producing and processing polyclonal sera are abundantly known in the art (e.g. Mayer and Walter, eds. Immunochemical Methods in Cell and Molecular Biology, Academic Press, London, 1987). Animals suitable for raising the antibodies are e.g. cows, rabbits, mice and chickens. Efficient methods for obtaining bovine antibodies against Campylobacter are described by Hilpert et al., 1987, J. Inf. Diseases 156: 158–166. Another attractive way of producing large amounts of antibodies i.e. production in egg yolk has been described by Hatta et al., 1993, Biosci. Biotech. Biochem. 57: 450–454.

Another embodiment of the present invention relates to the use of antibodies against a flagella-less *Campylobacter jejuni* strain for the preparation of a vaccine against *Campylobacter jejuni* colonisation.

Even more surprisingly, the following was found: antiserum raised against flagellaless *Campylobacter jejuni* mutants recognises three major protein bands, a 97 kD (+/−5 kD), a 60 kD (+/−5 kD) band and a 13 kD (+/−3 kD) band, on a Western blot of total *Campylobacter jejuni* protein, that are not seen when using antiserum against wild type *Campylobacter jejuni*. This phenomenon is equally seen in Western blots of wild type Campylobacter and of flagellaless Campylobacter. Thus, the three proteins are equally present in wild type and flagellaless Campylobacter strains. It was therefore concluded that the recognition of these specific proteins by the immune system only occurs on the absence of the flagella.

As mentioned above, antiserum against flagellaless Campylobacter mutants is capable of eliminating Campylobacter from the ceca below the level of detection. This antiserum differs from antiserum against wild type Campylobacter (not capable of eliminating Campylobacter) in that it additionally comprises antibodies against the 97 kD, 60 kD and 13 kD proteins. These three proteins apparently only induce antibodies if the flagella is absent, so it was concluded that these three proteins are capable of inducing antibodies that play an essential role in the elimination of Campylobacter from the ceca. Therefore, antibodies raised against either the 97 kD, the 60 kD or the 13 kD protein or a combination thereof are equally capable of eliminating Campylobacter strains from the ceca.

Thus another embodiment of the invention relates to antigenic proteins having a molecular weight of 97 kD, 60 kD or 13 kD, that are visible in a Western blot of *Campylobacter jejuni* protein after incubation of that Western blot with antibodies against a flagellaless mutant of *Campylobacter jejuni* and that are not visible after incubation of that blot with antibodies against wild type *Campylobacter jejuni*.

The 60 kD protein and the 13 kD protein have been further analysed and their amino acid sequence has been determined.

The amino acid sequence of the 60 kD protein is given below, and is also depicted in SEQ ID NO 1.

The amino acid sequence of the 60 kD protein is: "MAKEIIFSDEARNKLYEGVKKLN-DAVKVTMGPRGRNVLIQKSFGAPSIT-KDGVSVAKEVELKDSLENMGASLVRE-VASKTADQAGDGTTTATVLAHAIFKEGLRNITAGA NPIEVKRGMDKACEAI-VAELKKLSREVKDKKEIAQVATISANS- DEKIGNLIA-
DAMEKVGKDGVITVEEPKSINDELNVVEGMQFDR
GYLSPYFITNAEKMTVELSSPYILLFDK-
KITNLKDLLPVLEQIQKTGKPLLII-
AEDIEGEALATLVVNKLRGV-
LNISAVKAPGFGDRRKAMLEDIAILTGGEVISEELGR
TLESATIQDLGQASSVIIDKDNTTIVN-
GAGE1ANIDARVNQIKAQIAETTSDY-
DREKLQERLAKLSGGVAVIKVGATTE-
TEMKEKKDRVDDALSATKAAVEEGIVIGGGAALIK
AKAKIKLDLQGDEAIGAAIVERALRAPL-
RQIAENAGFDAGVVVNSVENAKDENTG-
FDAAKGEYVNMLESGIIDPVKVERVAL-
LNAVSVASMLLTTEATISEIKEDKPTMPDMSGMGG
MGGMGGMM"

The amino acid sequence of the 13 kD protein is given below and in SEQ ID NO 2. The amino acid sequence of this protein is: "MAISKEDVLEYISNLSVLELSELVKE-
FEEKFGVSAAPVMVAGGAVAG-
GAVAAAEEKTEFDIVLTDGGAKKIEVI-
KIVRALTGLGLKEAKDAVEQTPSTLKEGVAKAEAE
EAKKQLEEAGAKVELK"

There may be slight modifications in the amino acid sequence of the 60 kD and 13 kD protein. Variation in amino acid sequence may be the result of replacement of one or more amino acids by functional equivalents. Replacement by functional equivalents is often seen. Examples described by Neurath et al (The Proteins, Academic Press, New York (1979), page 14, FIG. 6) are i.a. the replacement of the amino acid alanine by serine; Ala/Ser, or Val/Ile, Asp/Glu, etc. In addition to the variations leading to replacement by functional equivalent amino acids mentioned above, variations may be found, in which an amino acid has been replaced by another amino acid that is not a functional equivalent. This kind of variation only differs from replacement with functional equivalents in that it may yield a protein that has a slight modification in its spatial folding. Both types of variation are often seen in proteins, and they are known as biological variations.

It goes without saying, that variations in the amino acid sequence of the 60 kD and 13 kD protein in such a way that the immunogenic activity of the polypeptide is retained, are also within the scope of the present invention.

The 97 kD, 60 kD or 13 kD proteins can be used to produce antibodies, which may be polyclonal, monospecific or monoclonal (or derivatives thereof). The 97 kD, 60 kD and 13 kD protein can be isolated according to many standard protein isolation procedures well-known in the art. One very easy method is the excision of these proteins from a preparative gel. If polyclonal antibodies are desired, techniques for producing and processing polyclonal sera are known in the art (e.g. Mayer and Walter, eds., see above). Monoclonal antibodies, reactive-against the 97 kD, 60 kD or 13 kD proteins according to the invention (or variants or fragments thereof), can be prepared by immunising inbred mice by techniques known in the art (Kohler and Milstein, Nature, 256, 495–497, 1975).

One of the advantages of using antibodies against any of these three proteins instead of antiserum against the whole flagellaless Campylobacter is, that specific monoclonal antibodies against these three proteins can easily be obtained from large scale hybridoma growth in fermentors. This allows the production of large amounts of antibodies at low cost/efforts and without the use of animals.

Thus, another embodiment of the invention relates to vaccines comprising antibodies against the 97 kD, 60 kD or 13 kD proteins of Campylobacter.

Even still another embodiment of the present invention relates to the use of antibodies against the 97 kD and/or 60 kD and/or 13 kD protein according to the invention for the preparation of a vaccine against *Campylobacter jejuni* colonisation.

The methods for the preparation of a vaccine according to the invention need not be complex. In principle, it suffices to raise antibodies against a flagella-less mutant or against the 97 kD and/or 60 kD and/or 13 kD protein in e.g. an animal, followed by collecting the blood and isolating the antiserum according to standard techniques. Suitable animals for raising such antibodies are e.g. rabbits and chickens. When chickens are used, antibodies can alternatively be obtained from the egg yolk of systemically immunised chickens. In principle the antibodies need not be diluted. They can be given as such, or if necessary even in a concentrated form. Alternatively, if the antibody concentration is very high, the thus obtained antiserum can e.g. be diluted before administration.

Thus, another embodiment of the present invention relates to methods for the preparation of a vaccine according to the invention. Such methods comprise raising antibodies against antigenic material of a flagellaless *Campylobacter jejuni* strain in a host animal followed by isolating the antibodies. In principle, this method will usually comprise the taking of blood from the host animal followed by purifying the antiserum, e.g. by centrifugation or filtration.

It is also possible to obtain cells that produce the desired antibodies, directed against the 97 kD, 60 kD and 13 kD proteins and to grow these in e.g. a fermentor. Antibodies can be harvested afterwards and they can be mixed, if necessary, with a pharmaceutically acceptable carrier. The advantage of such a method is that no animals need to be used for the preparation of the antibodies.

The invention is i.a. very suitable for treating broiler chicken, before slaughtering. Such broilers are usually slaughtered at six weeks of age. Therefore, treatment of the animals with the vaccine according to the invention at about one week before they are slaughtered causes a significant decrease in the level of Campylobacter-contamination. It is clear that the amount of vaccine to be given depends highly on the concentration of antibodies in the vaccine. As an indication may serve that very suitable amounts of antibodies are present in between 0.1 and 1 ml of crude antiserum. Antibody-titres in e.g. egg-yolk preparations can easily be determined by standard techniques well-known in the art, such as the ELISA technique.

The antibodies can easily be given as a rather crude preparation. A possible way of administration is e.g. feeding crude antiserum to chickens. Alternative routes of administration are e.g. admixing the serum with drinking water. Also, antibodies can be mixed directly with chicken food. For such purposes, an alternative is freeze-drying of the antibodies, thus enhancing their long term stability, before mixing them with the food or water. Also, the antibodies can be encapsulated before adding them to chicken food.

Still another embodiment of the invention provides an alternative for using antiserum or antibodies according to the invention for vaccination purposes. Alternatively, it is possible to use the 97 kD, 60 kD or 13 kD protein according to the invention directly for vaccination purposes. When the 97 kD, 60 kD or 13 kD protein are administered directly to poultry, they induce antibodies against the 97 kD, 60 kD or 13 kD protein directly. The animals then produce their own protective antibodies against Campylobacter. Again, this is surprising: administration of whole wild type Campylobacter strains does not lead to elimination of Campylobacter from the ceca, because wild type Campylobacter strains suppress the induction of antibodies against the 97 kD, 60 kD and 13 kD proteins. Thus, when the 97 kD, 60 kD and 13 kD protein are not given in an isolated form, but as a part of the whole wild type Campylobacter cell, they have no effect. Thus, another embodiment relates to vaccines comprising the specific antigenic 97 kD, 60 kD or 13 kD protein that is visible in a Western blot of *Campylobacter jejuni* protein after incubation of that Western blot with antibodies against a flagellaless mutant of *Campylobacter jejuni* and that is not visible after incubation of that blot with antibodies against wild type *Campylobacter jejuni.*

Such a vaccine can easily be prepared by admixing the protein with a pharmaceutically acceptable carrier. A pharmaceutically acceptable carrier is understood to be a compound that does not adversely effect the health of the animal to be vaccinated, at least not to the extend that the adverse effect is worse than the effects seen when the animal is not vaccinated. A pharmaceutically acceptable carrier can be e.g. sterile water or a sterile physiological salt solution. In a more complex for, the carrier can e.g. be a buffer.

Still another embodiment of the present invention relates to the antigenic 97 kD, 60 kD or 13 kD protein according to the invention for use in a vaccine.

A prefered form of this embodiment relates to the use of the antigenic 97 kD, 60 kD or 13 kD protein according to the invention for the manufacturing of a pharmaceutical composition for combating *Campylobacter jejuni* colonisation.

Suitable amounts of protein for the preparation of vaccines vary according to the way of administration. For systemic application, amounts between 1 and 1000 μg are very suitable. In vaccines for oral administration the amount may also be in this range. If however oral vaccination through drinking water is envisaged, possibly larger amounts of protein have to be given, due to spillage of water.

The vaccine according to the present invention may in a preferred presentation also contain an adjuvant. Adjuvants in general comprise substances that boost the immune response of the host in a nonspecific manner. A number of different adjuvants are known in the art. Examples of adjuvants are Freunds Complete and Incomplete adjuvant, vitamin E, non-ionic block polymers and polyamines such as dextransulphate, carbopol and pyran. Also very suitable are surface active substances such as Span, Tween, hexadecylamine, lysolecitin, methoxyhexadecylglycerol and saponins (i.a. Quil A®. Furthermore, peptides such as muramyldipeptides, dimethylglycine, tuftsin, are often used. Next to these adjuvants, Immune-stimulating Complexes (ISCOMS), mineral oil e.g. Bayol® or Markol®, vegetable oils or emulsions thereof and Diluvac® Forte can advantageously be used. The vaccine may also comprise a so-called "vehicle". A vehicle is a compound to which the polypeptide adheres, without being covalently bound to it. Often used vehicle compounds are e.g. aluminium hydroxide, -phosphate, sulphate or -oxide, silica, Kaolin, and Bentonite. A special form of such a vehicle, in which the antigen is partially embedded in the vehicle, is the so-called ISCOM (EP 109.942, EP 180.564, EP 242.380).

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), skimmed milk, gelatin, bovine serum albumin, carbohydrates e.g. sorbitol, mannitol, trehalose, starch, sucrose, dextran or glucose, proteins such as albumin or casein or degradation products thereof, and buffers, such as alkali metal phosphates. Freeze-drying is an efficient method for conservation. Freeze-dried material can be stored stable for many years. Storage temperatures for freeze-dried material may well be above zero degrees, without being detrimental to the material.

Freeze-drying can be done according to all well-known standard freeze-drying procedures.

Vaccines comprising the 97 kD, 60 kD or 13 kD protein are preferably administered mucosally. This can e.g. by done by oral administration, through admixing of the vaccine with drinking water. Especially for poultry, additional methods such as intra-ocular vaccination and intranasal vaccination are also very suitable ways of mucosal vaccination.

EXAMPLES

Example 1

Detection of a 97 kD, a 60 kD and a 13 kD Protein

Bacterial Strains:

Wild type 81116: *Campylobacter jejuni*, wild type, human isolate, flagellum phenotype $A^+B^+$, motile and invasive in vitro (Wassenaar, T. M., Bleumink-Pluym, N. M. C. and van derZeijst, B. A. M. 1991, EMBO Journal 10:2055–2061).

Mutant 81116-R2: FlaA and flaB deletion mutant (+kanamycin insert), flagellum phenotype $A^-B^-$, not motile and not invasive in vitro (Wassenaar, T. M., Bleumink-Pluym, N. M. C. and van der Zeijst, B. A. M. 1991, EMBO Journal 10:2055–2061).

Cell growth: Strain *Campylobacter jejuni* 81116 was inoculated on Blaser Campylobacter agar and strain *Campylobacter jejuni* 81116-R2 was inoculated on Blaser Campylobacter agar+40 μg/ml kanamycin. Plates were incubated for 48 hours at 41 degrees C. under microaerophilic conditions. A small number of colonies from the agar plates were inoculated in Brucella broth+1% yeast extract for strain 81116 and in Brucella broth+1% yeast extract+40 μg/ml kanamycin for strain 81116-2R. After incubation for 24 hours at 41 degrees C. under microaerophilic conditions, cultures were checked for the total number of bacteria and 0.2% formalin was added for inactivation (room temperature for 24 hours). Inactivated bacteria were collected by centrifugation. Cell pellets were resuspended in 0.01 M Tris pH 7.4 to a protein concentration of 1.0 mg/ml.

Then for standard PAAGE, 20 μl of this suspension was added per slot and run, on NuPage gel 4–12% Bis-Tris. Western blotting was done with NuPage transfer buffer/10% methanol.

For 2-D gel electrophoresis, standard methods as described by Adessi, C. (Electrophoresis 1997, 18 127–135) and by Görg, A., (Electrophoresis 1995, 16, 1079–1086) and the Instruction Manual 18-1038-63 of Pharmacia were used.

Preparation of Chicken Antisera.

4-Weeks-old chickens were IM vaccinated with 1 ml whole cell vaccine (see below) of strain 81116 or 81116-R2. One group of chickens was left unvaccinated. At 4 weeks after vaccination all chickens were bled to death. Sera were pooled per group and used for immunisation of 4-days-old chickens.

Sera thus obtained were diluted 20, 200 or 400 times and incubated with the Western blot according to standard methods.

Results: The left Western blot of FIG. 1 comprises total antigen of wild type Campylobacter strain 81116, the right Western blot comprises antigen of flagellaless Campylobacter strain 81116-2R. Lanes 1 and 7, lanes 2 and 8, and lanes 3 and 9 were incubated with 20, 200 or 400 times diluted antiserum against wild type Campylobacter strain 81116 respectively. Lanes 4 and 10, lanes 5 and 11, and lanes 6 and 12 were incubated with 20, 200 or 400 times diluted antiserum against flagellaless Campylobacter strain 81116-2R respectively.

As can be clearly seen in lanes 4–6 and lanes 10–12, two bands are visible with molecular weights of 97 and 60 kD respectively, that are not visible in lanes 1–3 and 7–9. (the somewhat fainter and more diffuse bands in between these lanes are molecular weight markers).

Figure 2:
FIG. 2. 2-D gel of total antigen of wild type Campylobacter strain 81116.
Figure 3A:
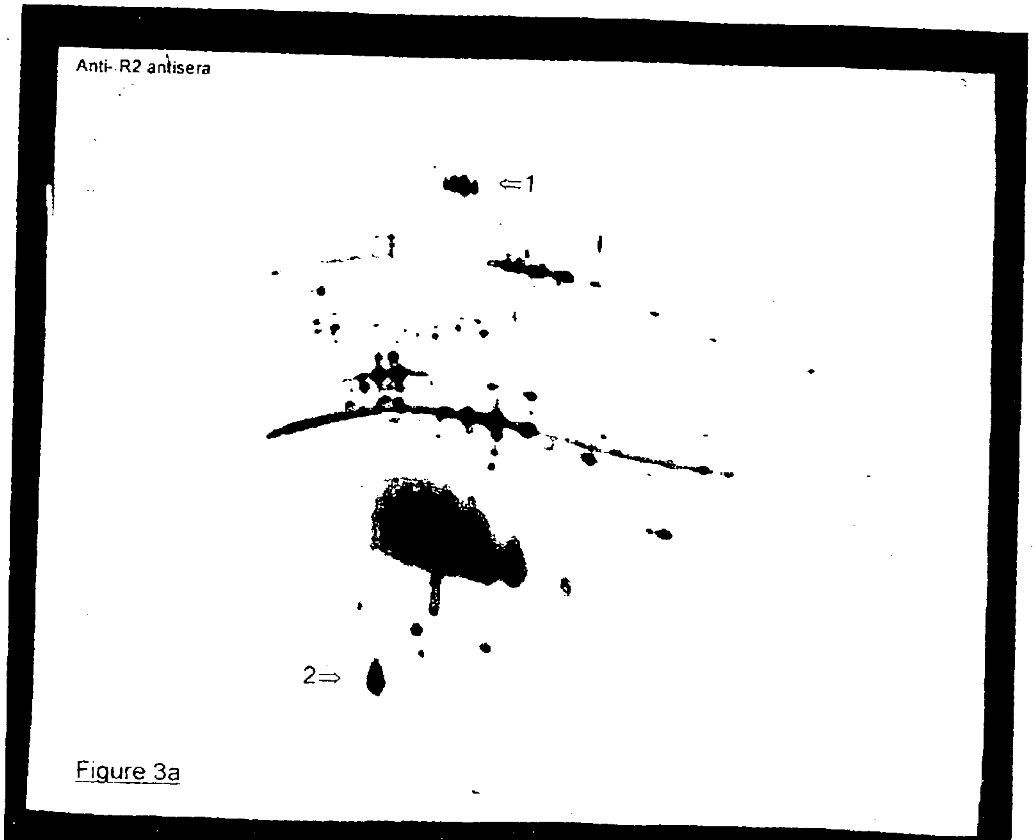
FIG. 3*a*. Western blot of the 2-D gel incubated with antiserum against flagellaless Campylobacter strain 81116-2R. The 60 kD protein is indicated by arrow 1, the 13 kD protein by arrow 2.
Figure 3B:
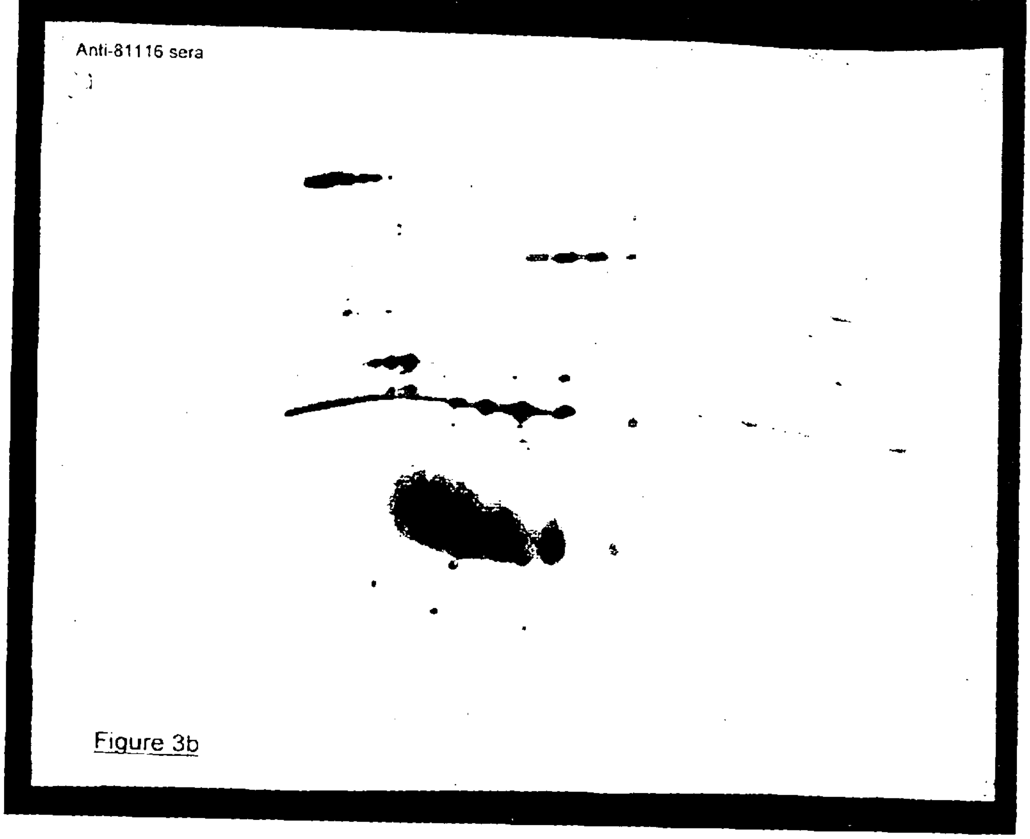
FIG. 3*b*. Western blot of the 2-D gel incubated with antiserum against wild-type Campylobacter strain 81116.

FIG. 2 shows a 2-D gel comprising total antigen of wild type Campylobacter strain 81116. A 2-D gel is better suitable for the detection of smaller proteins, and therefore, it is more suitable than standard 1-D PAAGE for detecting the presence of (antibodies against) the 13 kD protein. FIG. 3 shows Western blots of this gel. Blotting/incubation procedures were standard procedures comparable to those used for FIG. 1. FIG. 3*a* shows a Western blot of the 2-D gel incubated with antiserum against flagellaless Campylobacter strain 81116-2R. FIG. 3*b* shows the same Western blot, now incubated with antiserum against wild-type Campylobacter strain 81116. The Western blot in FIG. 3*a* clearly shows the presence of the antibodies against the 60 kD (arrow 1) and 13 kD protein (arrow 2) in serum raised against the flagellaless Campylobacter, and not found in serum raised against the wild-type Campylobacter (FIG. 3*b*).

These Western blots clearly show that flagellaless Campylobacter strains are capable of inducing an immune response against a 97 kD, a 60 kcD and a 13 kD protein, whereas wild type Campylobacter strains do not show this phenomenon.

Example 2

Preparation of Vaccines

Bacterial Strains:

Wild type 81116: see above.

Mutant 81116-R2: see above.

Preparation of Chicken Antisera for Passive Immunisation.

4-Weeks-old chickens were IM vaccinated with 1 ml whole cell vaccine (see below) of strain 81116 or 81116-R2. One group of chickens-was left unvaccinated. At 4 weeks after vaccination all chickens were bled to death. Sera were pooled per group and used for immunisation of 4-days-old chickens.

Preparation of Inactivated Whole Cell Vaccines.

Strain *Campylobacter jejuni* 81116 was inoculated on Blaser Campylobacter agar and strain *Campylobacter jejuni* 8111 6-R2 was inoculated on Blaser Campylobacter agar+40 μg/ml kanamycin. Plates were incubated for 48 hours at 41 ° C. under microaerophilic conditions. Colonies from the agar plates were inoculated in Brucella broth+1% yeast extract for strain 81116 and in Brucella broth+1% yeast extract+40 μg/ml kanamnycin for strain R2. After incubation for 24 hours at 41° C. under microaerophilic conditions, cultures were checked for the total number of bacteria and 0.2% formalin was added for inactivation (room temperature during 24 hours). Inactivated bacteria were collected by centrifugation, suspended in PBS and used for vaccine preparation by mixing cells and a Freunds Incomplete type of water in oil emulsion. The vaccine emulsions contain approximately $10^9$ bacteria per ml.

Preparation of Campylobacter Challenge Strain.

Strain *Campylobacter jejuni* 81116 was grown on Blaser Campylobacter agar plates at 41° C. for 48 hours under microaerophilic conditions. The growth of one plate was suspended in Brucella broth+1% Yeast extract and incubated at 41° C. for 48 hours in a closed bottle. Chickens were challenged orally with 0.2 ml culture. Viability count of the challenge culture was determined by plate counting.

Example 3

Vaccination Experiments

In this experiment, a comparison is made between passive vaccination with antiserum against wild type Campylobacter and against flagella-less Campylobacter, and active vaccination with an inactivated wild type Campylobacter whole cell preparation.

Chickens

Four-days-old or two-weeks-old SPF chickens.

Experimental Design Experiment 1.

Four groups of ten 4-days-old chickens were (once daily) treated orally with 0.8 ml chicken antiserum to wild type Campylobacter strain 81116, or with 0.8 ml chicken antiserum to the flagellaless mutant 81116-R2 or with 0.8 ml unvaccinated control chicken serum, or were left untreated as control. The first day (i.e. at 4-days of age) chicken received antisera just before challenge with $3.2\times10^7$ CFU/ml, as well as 6 hours after challenge. Treatments were continued until necropsy. At 5 or 10 days after challenge 5 birds of each group were killed and the CFU per gram cecal content was determined (see below: Post-mortem and bacteriology).

Experimental Design Experiment 2.

Four groups of ten 4-days-old chickens were (once daily) treated orally with 0.8 ml chicken antiserum to wild type Campylobacter strain 81116, or with chicken antiserum to the flagellaless mutant strain 81116-R2 or with unvaccinated control chicken serum or were left untreated. The first day (i.e. at 4 days of age) antisera were given just before challenge with $1.4\times10^8$ CFU/ml, as well as 6 hours after challenge. Treatments were continued until necropsy. At 5 days after challenge the chickens were killed and the CFU per gram cecal content was determined.

Experimental Design Experiment 3.

Three groups of 10 two-weeks-old chickens were vaccinated IM with 1 ml of the whole cell vaccines in a Freunds Incomplete type of water in oil emulsion, containing inactivated cells of wild type Campylobacter strain 81116 or the flagellaless mutant strain 81116-R2 or were left unvaccinated. At 5 weeks of age all chickens were challenged orally with wild type Campylobacter strain 81116, $1.4\times10^8$ CFU/ml. One week after challenge the chickens were killed and the CFU per gram cecal content was determined.

Post-mortem and Bacteriology

Chickens were killed and the content of each caecum was gently removed, weighed and diluted to 0.1 g per ml in 0.04 M PBS. Serial 10-fold dilutions were then plated out on selective Blaser Campylobacter agar plates. After 48 hours of incubation at 41° C. under microaerophilic conditions, the CFU per gram cecal content was determined.

RESULTS

Experiment 1

From Table 1 it can be concluded that repeated daily passive immunisation with serum against wild type Campylobacter or with unvaccinated chicken control serum had no effect on cecal colonisation by wild type Campylobacter if compared to untreated control chickens (at 5 days as well as 10 days after challenge). All three groups showed high levels of cecal colonisation by Campylobacter (up to $>10^8$ CFU per gram cecal content). In sharp contrast, passive immunisation with antiserum according to the invention (i.e. raised against a flagella-negative mutant) resulted in elimination of wild type Campylobacter from the ceca (or prevented colonisation). A level of <3 means that the number of CFU/gram caecum content is below the level of detection.

Experiment 2

In this experiment testing was repeated (see Table 2). Again a strong reduction of cecal colonisation was found in chickens passively vaccinated with antiserum according to the invention (i.e. raised against a flagella-negative mutant): 6/10 chickens were completely negative and a mean reduction of >3 logs was found.

Experiment 3

Because literature indicated that active immunisation with wild type Campylobacter could result in maximally 2 logs reduction of Campylobacter colonisation (Widders, P. R., Perry, R., Muir, W. I., Husband, A. J. and Long, K. A., 1996, Br. Poultry Sci. 37:765–778. ), we tested and compared wild type and R2 based vaccines in an active protection model.

From the results (Table 3) it is clear that neither vaccine had an effect on cecal colonisation.

TABLE 1a

| Anti- | Reisolation of *C. jejuni* 81116, 5 days after challenge | | | |
|---|---|---|---|---|
| | Log CFU/gram caecum content | | | |
| serum | *C. jejuni* 81116 | *C. jejuni* R2 | Not vaccinated | No antiserum |
| Chicken | | | | |
| 1 | 8.1 | <3.0 | 7.8 | 7.6 |
| 2 | 5.9 | <3.0 | 8.7 | 5.6 |
| 3 | 8.5 | <3.0 | 8.1 | 9.1 |
| 4 | 5.5 | <3.0 | 7.7 | 7.2 |
| 5 | 8.6 | <3.0 | 7.6 | 8.8 |
| Mean | 7.3 | <3.0 | 8.0 | 7.7 |
| Sd | 1.5 | | 0.4 | 1.4 |

TABLE 1b

| Anti- | Reisolation of *C. jejuni* 81116, 10 days after challenge | | | |
|---|---|---|---|---|
| | Log CFU/gram caecum content | | | |
| serum | *C. jejuni* 81116 | *C. jejuni* R2 | Not vaccinated | No antiserum |
| Chicken | | | | |
| 1 | 9.0 | 3.5 | 7.8 | 8.1 |
| 2 | 9.1 | <3.0 | 8.9 | 7.6 |
| 3 | 9.0 | <3.0 | 9.3 | 7.4 |
| 4 | 9.1 | <3.0 | 7.0 | 7.8 |
| 5 | 8.5 | <3.0 | 8.7 | 8.2 |
| Mean | 8.9 | <3.1 | 8.3 | 7.8 |
| Sd | 0.3 | 0.2 | 0.9 | 0.3 |

TABLE 2

| Anti- | Reisolation of *C. jejuni* 81116, 5 days after challenge | | | |
|---|---|---|---|---|
| | Log CFU/gram caecum content | | | |
| serum | *C. jejuni* 81116 | *C. jejuni* R2 | Not vaccinated | No antiserum |
| Chicken | | | | |
| 1 | 7.5 | 3.8 | 9.5 | <3.0 |
| 2 | <3.0 | 9.1 | 7.9 | 7.5 |
| 3 | 7.4 | 8.9 | 7.6 | 7.9 |
| 4 | 7.5 | 6.0 | 8.4 | 8.5 |
| 5 | 6.0 | <3.0 | 7.3 | 9.0 |
| 6 | 9.1 | <3.0 | 7.0 | 5.8 |
| 7 | 8.9 | <3.0 | 6.6 | 9.0 |
| 8 | 7.6 | <3.0 | 9.1 | 7.0 |
| 9 | <3.0 | <3.0 | 7.5 | 9.0 |
| 10 | <3.0 | <3.0 | 9.4 | 9.8 |
| Mean | <6.3[a] | <4.6[b] | 8.0 | <7.7 |
| Sd | 2.4 | 2.5 | 1.0 | 2.0 |

[a] $p \leqq 0.05$ compared to the group receiving antiserum of not vaccinated chickens (two sample t-tests)

[b] $p \leqq 0.001$ compared to the group receiving antiserum of not vaccinated chickens (two sample t-tests)

TABLE 3

| Reisolation of *C. jejuni* 81116, 6 days after challenge. | | | |
|---|---|---|---|
| | Log CFU/gram caecum content | | |
| Chicken | Vaccination with *C. jejuni* 81116 | Vaccination with *C. jejuni* R2 | Not vaccinated |
| 1 | 8.3 | 5.2 | 8.3 |
| 2 | 8.7 | 8.0 | 8.7 |
| 3 | | 8.7 | |
| 4 | 7.1 | 8.5 | 7.1 |
| 5 | 8.1 | 7.8 | 8.1 |
| 6 | 8.4 | | 8.4 |
| 7 | 7.7 | 7.8 | 7.7 |
| 8 | 8.5 | 8.8 | 8.5 |
| 9 | 9.1 | 8.3 | 9.1 |
| 10 | 7.5 | 7.4 | 7.5 |
| Mean | 8.2 | 7.8 | 8.2 |
| Std. | 0.6 | 1.1 | 0.6 |

Conclusion:

Vaccines based upon antibodies raised against flagellaless Campylobacter are capable of eliminating wild-type Campylobacter from the caecum. This is in sharp contrast to their counterparts having antibodies raised against wild type Campylobacter. It is also in sharp contrast to vaccines comprising wild type Campylobacter cells.

What is claimed is:

1. A vaccine for the prevention of Campylobacter colonization in animals consisting essentially of an effective amount of chicken antiserum raised against a flagellaless Campylobacter strain wherein the antiserum recognizes a 97 kD (+/−5 kD), a 60 kD (+/−5 kD), and a 13 kD (+/−3 kD) band on a Western Blot, the vaccine essentially free of anti-flagellar antibodies.

2. A vaccine according to claim 1 wherein the flagellaless Campylobacter strain is *campylobacter jejuni.*

3. A vaccine according to claim 2 wherein the flagellaless *Campylobacter jejuni* strain is strain R2.

4. A vaccine for the prevention of *Campylobacter jejuni* colonization in poultry comprising an effective amount of chicken antibodies against the antigenic protein consisting essentially of a protein of a Campylobacter having a molecular weight of 97 kD (+/−5kD), whereby it is visible in a Western blot with antibodies against a flagellaless mutant of *Campylobacter jejuni* and that it is not visible after incubation of said blot with antibodies against the wild type *Campylobacter jejuni*, the vaccine essentially free of anti-flagellar antibodies.

* * * * *

SEQUENCE LISTING

```
<160> NUMBER OF SEQ ID NOS:  2

<210> SEQ ID NO 1
<211> LENGTH: 125
<212> TYPE: PRT
<213> ORGANISM: Campylobacter jejuni

<400> SEQUENCE: 1

Met Ala Ile Ser Lys Glu Asp Val Leu Glu Tyr Ile Ser Asn Leu Ser
  1               5                  10                  15

Val Leu Glu Leu Ser Glu Leu Val Lys Glu Phe Glu Glu Lys Phe Gly
             20                  25                  30

Val Ser Ala Ala Pro Val Met Val Ala Gly Gly Ala Val Ala Gly Gly
         35                  40                  45

Ala Val Ala Ala Ala Glu Glu Lys Thr Glu Phe Asp Ile Val Leu Thr
     50                  55                  60

Asp Gly Gly Ala Lys Lys Ile Glu Val Ile Lys Ile Val Arg Ala Leu
 65                  70                  75                  80

Thr Gly Leu Gly Leu Lys Glu Ala Lys Asp Ala Val Glu Gln Thr Pro
                 85                  90                  95

Ser Thr Leu Lys Glu Gly Val Ala Lys Ala Glu Ala Glu Glu Ala Lys
            100                 105                 110

Lys Gln Leu Glu Glu Ala Gly Ala Lys Val Glu Leu Lys
        115                 120                 125


<210> SEQ ID NO 2
<211> LENGTH: 545
<212> TYPE: PRT
<213> ORGANISM: Campylobacter jejuni

<400> SEQUENCE: 2

Met Ala Lys Glu Ile Ile Phe Ser Asp Glu Ala Arg Asn Lys Leu Tyr
  1               5                  10                  15

Glu Gly Val Lys Lys Leu Asn Asp Ala Val Lys Val Thr Met Gly Pro
             20                  25                  30

Arg Gly Arg Asn Val Leu Ile Gln Lys Ser Phe Gly Ala Pro Ser Ile
         35                  40                  45

Thr Lys Asp Gly Val Ser Val Ala Lys Glu Val Glu Leu Lys Asp Ser
     50                  55                  60

Leu Glu Asn Met Gly Ala Ser Leu Val Arg Glu Val Ala Ser Lys Thr
 65                  70                  75                  80

Ala Asp Gln Ala Gly Asp Gly Thr Thr Thr Ala Thr Val Leu Ala His
                 85                  90                  95

Ala Ile Phe Lys Glu Gly Leu Arg Asn Ile Thr Ala Gly Ala Asn Pro
            100                 105                 110

Ile Glu Val Lys Arg Gly Met Asp Lys Ala Cys Glu Ala Ile Val Ala
        115                 120                 125

Glu Leu Lys Lys Leu Ser Arg Glu Val Lys Asp Lys Lys Glu Ile Ala
    130                 135                 140

Gln Val Ala Thr Ile Ser Ala Asn Ser Asp Glu Lys Ile Gly Asn Leu
145                 150                 155                 160

Ile Ala Asp Ala Met Glu Lys Val Gly Lys Asp Gly Val Ile Thr Val
                165                 170                 175

Glu Glu Pro Lys Ser Ile Asn Asp Glu Leu Asn Val Val Glu Gly Met
            180                 185                 190
```

-continued

```
Gln Phe Asp Arg Gly Tyr Leu Ser Pro Tyr Phe Ile Thr Asn Ala Glu
        195                 200                 205

Lys Met Thr Val Glu Leu Ser Ser Pro Tyr Ile Leu Leu Phe Asp Lys
    210                 215                 220

Lys Ile Thr Asn Leu Lys Asp Leu Leu Pro Val Leu Glu Gln Ile Gln
225                 230                 235                 240

Lys Thr Gly Lys Pro Leu Leu Ile Ile Ala Glu Asp Ile Glu Gly Glu
                245                 250                 255

Ala Leu Ala Thr Leu Val Val Asn Lys Leu Arg Gly Val Leu Asn Ile
            260                 265                 270

Ser Ala Val Lys Ala Pro Gly Phe Gly Asp Arg Arg Lys Ala Met Leu
        275                 280                 285

Glu Asp Ile Ala Ile Leu Thr Gly Gly Glu Val Ile Ser Glu Glu Leu
    290                 295                 300

Gly Arg Thr Leu Glu Ser Ala Thr Ile Gln Asp Leu Gly Gln Ala Ser
305                 310                 315                 320

Ser Val Ile Ile Asp Lys Asp Asn Thr Thr Ile Val Asn Gly Ala Gly
                325                 330                 335

Glu Lys Ala Asn Ile Asp Ala Arg Val Asn Gln Ile Lys Ala Gln Ile
            340                 345                 350

Ala Glu Thr Thr Ser Asp Tyr Asp Arg Glu Lys Leu Gln Glu Arg Leu
        355                 360                 365

Ala Lys Leu Ser Gly Gly Val Ala Val Ile Lys Val Gly Ala Thr Thr
    370                 375                 380

Glu Thr Glu Met Lys Glu Lys Lys Asp Arg Val Asp Asp Ala Leu Ser
385                 390                 395                 400

Ala Thr Lys Ala Ala Val Glu Glu Gly Ile Val Ile Gly Gly Gly Ala
                405                 410                 415

Ala Leu Ile Lys Ala Lys Ala Lys Ile Lys Leu Asp Leu Gln Gly Asp
            420                 425                 430

Glu Ala Ile Gly Ala Ala Ile Val Glu Arg Ala Leu Arg Ala Pro Leu
        435                 440                 445

Arg Gln Ile Ala Glu Asn Ala Gly Phe Asp Ala Gly Val Val Val Asn
    450                 455                 460

Ser Val Glu Asn Ala Lys Asp Glu Asn Thr Gly Phe Asp Ala Ala Lys
465                 470                 475                 480

Gly Glu Tyr Val Asn Met Leu Glu Ser Gly Ile Ile Asp Pro Val Lys
                485                 490                 495

Val Glu Arg Val Ala Leu Leu Asn Ala Val Ser Val Ala Ser Met Leu
            500                 505                 510

Leu Thr Thr Glu Ala Thr Ile Ser Glu Ile Lys Glu Asp Lys Pro Thr
        515                 520                 525

Met Pro Asp Met Ser Gly Met Gly Gly Met Gly Gly Met Gly Gly Met
    530                 535                 540

Met
545
```